US010428375B2

(12) United States Patent
Hopper

(10) Patent No.: US 10,428,375 B2
(45) Date of Patent: Oct. 1, 2019

(54) NUCLEIC ACID AMPLIFICATION AND DETECTION APPARATUS AND METHOD

(71) Applicant: Axxin Pty Ltd, Melbourne (AU)

(72) Inventor: William Robb Hopper, East Ivanhoe (AU)

(73) Assignee: AXXIN PTY LTD, Melbourne (AU)

(*) Notice: Subject to any disclaimer, the term of this patent is extended or adjusted under 35 U.S.C. 154(b) by 0 days.

(21) Appl. No.: 14/376,185

(22) PCT Filed: Feb. 1, 2013

(86) PCT No.: PCT/AU2013/000092
§ 371 (c)(1),
(2) Date: Aug. 1, 2014

(87) PCT Pub. No.: WO2013/113072
PCT Pub. Date: Aug. 8, 2013

(65) Prior Publication Data
US 2014/0377766 A1    Dec. 25, 2014

Related U.S. Application Data

(60) Provisional application No. 61/594,870, filed on Feb. 3, 2012.

(51) Int. Cl.
*C12Q 1/6851* (2018.01)
*G01N 21/64* (2006.01)
*B01L 7/00* (2006.01)

(52) U.S. Cl.
CPC ....... *C12Q 1/6851* (2013.01); *G01N 21/6452* (2013.01); *B01L 7/52* (2013.01)

(58) Field of Classification Search
CPC ..... C12Q 1/6851; G01N 21/6452; B01L 7/52; B01L 7/525; B01L 7/5255
See application file for complete search history.

(56) References Cited

U.S. PATENT DOCUMENTS 4,234,540 A    11/1980   Ginsberg et al.
4,250,266 A *  2/1981    Wade ................. C12M 23/04
                                                    204/403.02
(Continued)

FOREIGN PATENT DOCUMENTS

AU    2013202899 A1    5/2013
EP         1059523 B1    7/2007
(Continued)

OTHER PUBLICATIONS

Cikos et al.; Transformation of real-time PCR fluorescence data to target gene quantity; Analytical Biochemistry; 384(1); pp. 1-10; Jan. 1, 2009.
(Continued)

*Primary Examiner* — William H. Beisner
(74) *Attorney, Agent, or Firm* — Shay Glenn LLP

(57) ABSTRACT

A nucleic acid amplification and detection apparatus, including: a support configured to receive a plurality of reaction vessels containing respective samples of one or more nucleic acids to be amplified, the support being rotatable about an axis of rotation and the reaction vessels being received in the support at respective receiving locations distributed about the axis of rotation; a temperature control component thermally coupled to the support and configured to control the temperature of the support in order to amplify the nucleic acids contained in the reaction vessels while received in the support; one or more measurement components configured to measure one or more characteristics of the nucleic acids within the reaction vessels at respective measurement locations distributed about the axis of rotation; an actuator coupled to the support and configured to rotate the support about the axis of rotation; and a sample position controller coupled to the actuator and being configured to rotate the support about the axis of rotation so as to position a selected one of the plurality of reaction vessels to a selected one of (Continued)

the measurement locations to allow a corresponding one of the measurement components to perform a corresponding measurement on the corresponding sample.

17 Claims, 7 Drawing Sheets

(56) References Cited

U.S. PATENT DOCUMENTS

| | | | |
|---|---|---|---|
| 4,912,034 A | 3/1990 | Kalra et al. | |
| 5,152,965 A | 10/1992 | Fisk et al. | |
| 5,435,970 A | 7/1995 | Mamenta et al. | |
| 5,955,351 A | 9/1999 | Gerdes et al. | |
| 6,171,870 B1 | 1/2001 | Freitag | |
| 6,197,598 B1 | 3/2001 | Schrier et al. | |
| 8,895,296 B2 * | 11/2014 | Sano | G01N 21/645 422/82.08 |
| 2002/0031768 A1 * | 3/2002 | McMillan | C12Q 1/6851 435/6.11 |
| 2003/0129738 A1 | 7/2003 | Sorenson et al. | |
| 2003/0170686 A1 * | 9/2003 | Hoet | B03C 1/01 435/6.12 |
| 2004/0161788 A1 | 8/2004 | Chen et al. | |
| 2004/0265173 A1 * | 12/2004 | Matsumoto | G01N 35/025 422/64 |
| 2005/0033196 A1 | 2/2005 | Alroy | |
| 2005/0142031 A1 | 6/2005 | Wickstead et al. | |
| 2005/0180891 A1 | 8/2005 | Webster et al. | |
| 2006/0030790 A1 | 2/2006 | Braig et al. | |
| 2006/0188392 A1 | 8/2006 | Tanaka et al. | |
| 2006/0223172 A1 * | 10/2006 | Bedingham | G01J 3/4406 435/288.7 |
| 2006/0270027 A1 * | 11/2006 | Shaw | B01L 1/02 435/303.3 |
| 2006/0275852 A1 | 12/2006 | Montagu et al. | |
| 2006/0275922 A1 | 12/2006 | Gould et al. | |
| 2006/0292035 A1 | 12/2006 | Gould et al. | |
| 2007/0184492 A1 | 8/2007 | Wang et al. | |
| 2008/0020380 A1 | 1/2008 | Patno et al. | |
| 2008/0166820 A1 | 7/2008 | Gould et al. | |
| 2008/0199851 A1 | 8/2008 | Egan et al. | |
| 2008/0287308 A1 * | 11/2008 | Hubbell | G06F 19/18 506/8 |
| 2009/0181388 A1 | 7/2009 | You et al. | |
| 2009/0204997 A1 | 8/2009 | Xu et al. | |
| 2011/0039261 A1 | 2/2011 | Hillebrand et al. | |
| 2011/0283818 A1 | 11/2011 | Kramer | |
| 2012/0076693 A1 | 3/2012 | Hopper | |
| 2013/0309679 A1 | 11/2013 | Ismagilov et al. | |
| 2014/0194305 A1 | 7/2014 | Kayyem et al. | |
| 2017/0318802 A1 | 11/2017 | Hopper et al. | |
| 2018/0193831 A1 | 7/2018 | Hopper | |

FOREIGN PATENT DOCUMENTS

| | | | | |
|---|---|---|---|---|
| EP | 2123360 A1 * | 11/2009 | | B01L 7/52 |
| EP | 2163999 A2 | 3/2010 | | |
| JP | H08-43294 A | 2/1996 | | |
| WO | WO92/08986 A1 | 5/1992 | | |
| WO | WO99/57561 A2 | 11/1999 | | |
| WO | WO 2005/045408 A1 | 5/2005 | | |
| WO | WO2006/047777 A2 | 5/2006 | | |
| WO | WO2007/005077 A1 | 1/2007 | | |
| WO | WO2007/106579 A2 | 9/2007 | | |
| WO | WO2008/005248 A2 | 1/2008 | | |
| WO | WO 2009/011869 A1 | 1/2009 | | |
| WO | WO 2009/132268 A1 | 10/2009 | | |
| WO | WO2010/030686 A1 | 3/2010 | | |
| WO | WO2010/104478 A1 | 9/2010 | | |
| WO | WO2013/113054 A1 | 8/2013 | | |
| WO | WO2014/000037 A1 | 1/2014 | | |
| WO | WO2014/100732 A1 | 6/2014 | | |

OTHER PUBLICATIONS

Durtschi et al.; Evaluation of quantification methods for real-time PCR minor groove binding hybridization probe assays; Analytical Biochemistry; 361(1); pp. 55-64; Jan. 4, 2007.

Liu et al.; Progress curve analysis of qRT-PCR reactions using the logistic growth equation; Biotechnology Progress; 27(5); pp. 1407-1414; Sep. 15, 2011.

Pipper et al.; Clockwork PCR including sample preparation; Angew. Chem. Int. Ed.; 47(21); pp. 3900-3904; Apr. 15, 2008.

Gubala et al.; Point of care diagnostics: status and future; Analytical Chemistry; 84(2); pp. 487-515; Jan. 2012.

Wikipedia; Immunoassay; 4 pages; Feb. 24, 2015; retrieved from the internet (http://en.wikiopedia.org/wiki/Immunoassay).

Wikipedia; Lateral flow test; 4 pages; Feb. 24, 2015; retrieved from the internet (http:en.wikipedia.org/wiki/Lateral_flow_test).

Hopper; U.S. Appl. No. 14/411,203 entitled "Nucleic acid amplification and detection kit," filed Dec. 24, 2014.

Roche Diagnostics GMBH; LightCycler 480 Instrument Operator's Manual, Software version 1.5; © 2008; 8 pages; Oct. 15, 2014; retrieved from the internet (http://pedrovale.files.wordpress.com/2013/08/lightcyclerc2ae-480-instrument-operators-manual.pdf).

Wikipedia; Polymerase chain reaction; 13 pages; Oct. 15, 2014; retrieved from the internet (http://en.wikipedia.org/wiki/Polymerase_chain_reaction).

Wikipedia; Variants of PCR; 11 pages; Oct. 15, 2014; retrieved from the Internet (http://en.wikipedia.org/wiki/Variants_of_PCR#Isothermal_amplification_methods).

European Leukemia Network; Imatinib testing for CML; 7 pages; retrieved from the internet (https://www.eutos.org/content/molecular_monitoring/information/pcr_testing/index_eng.html); on Apr. 4, 2018.

Zhang et al.; Micropumps, microvalves, and micromixers within pcr microfludic chips: Advances and trends; Biotechnology Advances; 25(5); pp. 483-514; Sep. 1, 2007.

* cited by examiner

NUCLEIC ACID AMPLIFICATION AND DETECTION APPARATUS AND METHOD

TECHNICAL FIELD

The present invention relates to a nucleic acid amplification and detection apparatus and method.

BACKGROUND

The amplification of nucleic acids is important in many fields, including medical, biomedical, environmental, veterinary and food safety testing. In general, nucleic acids are amplified by one of two methods: polymerase chain reaction (PCR) or isothermal amplification, both of which are described below.

Polymerase Chain Reaction (PCR)

As described in the Wikipedia[1] at http://en.wikipedia.org/wiki/Polymerase_chain_reaction:

[1] The Wikipedia text quoted herein is released under CC-BY-SA, see http://creativecommons.org/licenses/by-sa/3.0.

"The polymerase chain reaction (PCR) is a scientific technique in molecular biology to amplify a single or a few copies of a piece of DNA across several orders of magnitude, generating thousands to millions of copies of a particular DNA sequence.

Developed in 1983 by Kary Mullis, PCR is now a common and often indispensable technique used in medical and biological research labs for a variety of applications. These include DNA cloning for sequencing, DNA-based phylogeny, or functional analysis of genes; the diagnosis of hereditary diseases; the identification of genetic fingerprints (used in forensic sciences and paternity testing); and the detection and diagnosis of infectious diseases. In 1993, Mullis was awarded the Nobel Prize in Chemistry along with Michael Smith for his work on PCR.

The method relies on thermal cycling, consisting of cycles of repeated heating and cooling of the reaction for DNA melting and enzymatic replication of the DNA. Primers (short DNA fragments) containing sequences complementary to the target region along with a DNA polymerase (after which the method is named) are key components to enable selective and repeated amplification. As PCR progresses, the DNA generated is itself used as a template for replication, setting in motion a chain reaction in which the DNA template is exponentially amplified. PCR can be extensively modified to perform a wide array of genetic manipulations.

Almost all PCR applications employ a heat-stable DNA polymerase, such as Taq polymerase, an enzyme originally isolated from the bacterium *Thermus aquaticus*. This DNA polymerase enzymatically assembles a new DNA strand from DNA building-blocks, the nucleotides, by using single-stranded DNA as a template and DNA oligonucleotides (also called DNA primers), which are required for initiation of DNA synthesis. The vast majority of PCR methods use thermal cycling, i.e., alternately heating and cooling the PCR sample to a defined series of temperature steps. These thermal cycling steps are necessary first to physically separate the two strands in a DNA double helix at a high temperature in a process called DNA melting. At a lower temperature, each strand is then used as the template in DNA synthesis by the DNA polymerase to selectively amplify the target DNA. The selectivity of PCR results from the use of primers that are complementary to the DNA region targeted for amplification under specific thermal cycling conditions.

PCR Principles and Procedure

PCR is used to amplify a specific region of a DNA strand (the DNA target). Most PCR methods typically amplify DNA fragments of up to ~10 kilo base pairs (kb), although some techniques allow for amplification of fragments up to 40 kb in size.

A basic PCR set up requires several components and reagents. These components include:
  DNA template that contains the DNA region (target) to be amplified.
  Two primers that are complementary to the 3' (three prime) ends of each of the sense and anti-sense strand of the DNA target.
  Taq polymerase or another DNA polymerase with a temperature optimum at around 70° C.
  Deoxynucleoside triphosphates (dNTPs; nucleotides containing triphosphate groups), the building-blocks from which the DNA polymerase synthesizes a new DNA strand.
  Buffer solution, providing a suitable chemical environment for optimum activity and stability of the DNA polymerase.
  Divalent cations, magnesium or manganese ions; generally $Mg^{2+}$ is used, but $Mn^{2+}$ can be utilized for PCR-mediated DNA mutagenesis, as higher $Mn^{2+}$ concentration increases the error rate during DNA synthesis.
  Monovalent cation potassium ions.

The PCR is commonly carried out in a reaction volume of 10-200 μl in small reaction tubes (0.2-0.5 ml volumes) in a thermal cycler. The thermal cycler heats and cools the reaction tubes to achieve the temperatures required at each step of the reaction (see below). Many modern thermal cyclers make use of the Peltier effect, which permits both heating and cooling of the block holding the PCR tubes simply by reversing the electric current. Thin-walled reaction tubes permit favorable thermal conductivity to allow for rapid thermal equilibration. Most thermal cyclers have heated lids to prevent condensation at the top of the reaction tube. Older thermocyclers lacking a heated lid require a layer of oil on top of the reaction mixture or a ball of wax inside the tube.

Procedure

Typically, PCR consists of a series of 20-40 repeated temperature changes, called cycles, with each cycle commonly consisting of 2-3 discrete temperature steps, usually three . . . . The cycling is often preceded by a single temperature step (called hold) at a high temperature (>90° C.), and followed by one hold at the end for final product extension or brief storage. The temperatures used and the length of time they are applied in each cycle depend on a variety of parameters. These include the enzyme used for DNA synthesis, the concentration of divalent ions and dNTPs in the reaction, and the melting temperature (Tm) of the primers.

Initialization step: This step consists of heating the reaction to a temperature of 94-96° C. (or 98° C. if extremely thermostable polymerases are used), which is held for 1-9 minutes. It is only required for DNA polymerases that require heat activation by hot-start PCR.
  Denaturation step: This step is the first regular cycling event and consists of heating the reaction to 94-98° C. for 20-30 seconds. It causes DNA melting of the DNA template by disrupting the hydrogen bonds between complementary bases, yielding single-stranded DNA molecules.

Annealing step: The reaction temperature is lowered to 50-65° C. for 20-40 seconds allowing annealing of the primers to the single-stranded DNA template. Typically the annealing temperature is about 3-5 degrees Celsius below the Tm of the primers used. Stable DNA-DNA hydrogen bonds are only formed when the primer sequence very closely matches the template sequence. The polymerase binds to the primer-template hybrid and begins DNA synthesis.

Extension/elongation step: The temperature at this step depends on the DNA polymerase used; Taq polymerase has its optimum activity temperature at 75-80° C., and commonly a temperature of 72° C. is used with this enzyme. At this step the DNA polymerase synthesizes a new DNA strand complementary to the DNA template strand by adding dNTPs that are complementary to the template in 5' to 3' direction, condensing the 5'-phosphate group of the dNTPs with the 3'-hydroxyl group at the end of the nascent (extending) DNA strand. The extension time depends both on the DNA polymerase used and on the length of the DNA fragment to be amplified. As a rule-of-thumb, at its optimum temperature, the DNA polymerase will polymerize a thousand bases per minute. Under optimum conditions, i.e., if there are no limitations due to limiting substrates or reagents, at each extension step, the amount of DNA target is doubled, leading to exponential (geometric) amplification of the specific DNA fragment.

Final elongation: This single step is occasionally performed at a temperature of 70-74° C. for 5-15 minutes after the last PCR cycle to ensure that any remaining single-stranded DNA is fully extended.

Final hold: This step at 4-15° C. for an indefinite time may be employed for short-term storage of the reaction.

To check whether the PCR generated the anticipated DNA fragment (also sometimes referred to as the amplimer or amplicon), agarose gel electrophoresis is employed for size separation of the PCR products. The size(s) of PCR products is determined by comparison with a DNA ladder (a molecular weight marker), which contains DNA fragments of known size, run on the gel alongside the PCR products . . . .

PCR Stages

The PCR process can be divided into three stages:

Exponential amplification: At every cycle, the amount of product is doubled (assuming 100% reaction efficiency). The reaction is very sensitive: only minute quantities of DNA need to be present.

Leveling off stage: The reaction slows as the DNA polymerase loses activity and as consumption of reagents such as dNTPs and primers causes them to become limiting.

Plateau: No more product accumulates due to exhaustion of reagents and enzyme.

PCR Optimization

In practice, PCR can fail for various reasons, in part due to its sensitivity to contamination causing amplification of spurious DNA products. Because of this, a number of techniques and procedures have been developed for optimizing PCR conditions. Contamination with extraneous DNA is addressed with lab protocols and procedures that separate pre-PCR mixtures from potential DNA contaminants. This usually involves spatial separation of PCR-setup areas from areas for analysis or purification of PCR products, use of disposable plasticware, and thoroughly cleaning the work surface between reaction setups. Primer-design techniques are important in improving PCR product yield and in avoiding the formation of spurious products, and the usage of alternate buffer components or polymerase enzymes can help with amplification of long or otherwise problematic regions of DNA. Addition of reagents, such as formamide, in buffer systems may increase the specificity and yield of PCR.

Amplification and Quantification of DNA

Because PCR amplifies the regions of DNA that it targets, PCR can be used to analyze extremely small amounts of sample. This is often critical for forensic analysis, when only a trace amount of DNA is available as evidence. PCR may also be used in the analysis of ancient DNA that is tens of thousands of years old. These PCR-based techniques have been successfully used on animals, such as a forty-thousand-year-old mammoth, and also on human DNA, in applications ranging from the analysis of Egyptian mummies to the identification of a Russian tsar.

Quantitative PCR methods allow the estimation of the amount of a given sequence present in a sample—a technique often applied to quantitatively determine levels of gene expression. Real-time PCR is an established tool for DNA quantification that measures the accumulation of DNA product after each round of PCR amplification.

PCR in Diagnosis of Diseases

PCR permits early diagnosis of malignant diseases such as leukemia and lymphomas, which is currently the highest-developed in cancer research and is already being used routinely. (See the studies cited in the EUTOS For CML study article at http://www.eutos.org/content/molecular_monitoring/information/per_testing/, especially notes 10-13.) PCR assays can be performed directly on genomic DNA samples to detect translocation-specific malignant cells at a sensitivity that is at least 10,000-fold higher than that of other methods.

PCR also permits identification of non-cultivatable or slow-growing microorganisms such as mycobacteria, anaerobic bacteria, or viruses from tissue culture assays and animal models. The basis for PCR diagnostic applications in microbiology is the detection of infectious agents and the discrimination of non-pathogenic from pathogenic strains by virtue of specific genes.

Viral DNA can likewise be detected by PCR. The primers used need to be specific to the targeted sequences in the DNA of a virus, and the PCR can be used for diagnostic analyses or DNA sequencing of the viral genome. The high sensitivity of PCR permits virus detection soon after infection and even before the onset of disease. Such early detection may give physicians a significant lead in treatment. The amount of virus ("viral load") in a patient can also be quantified by PCR-based DNA quantitation techniques (see below).

Isothermal Amplification Methods

As described in the Wikipedia[1] at http://en.wikipedia.org/wiki/Variants_of_PCR#Isothermal_amplification_methods:

"Some DNA amplification protocols have been developed that may be used alternatively to PCR:

Helicase-dependent amplification is similar to traditional PCR, but uses a constant temperature rather than cycling through denaturation and annealing/extension steps. DNA Helicase, an enzyme that unwinds DNA, is used in place of thermal denaturation.

PAN-AC also uses isothermal conditions for amplification, and may be used to analyze living cells.

Nicking Enzyme Amplification Reaction referred to as NEAR, is isothermal, replicating DNA at a constant temperature using a polymerase and nicking enzyme.

Recombinase Polymerase Amplification (RPA). The method uses a recombinase to specifically pair primers with double-stranded DNA on the basis of homology, thus directing DNA synthesis from defined DNA sequences present in the sample. Presence of the target sequence initiates DNA amplification, and no thermal or chemical melting of DNA is required. The reaction progresses rapidly and results in specific DNA amplification from just a few target copies to detectable levels typically within 5-10 minutes. The entire reaction system is stable as a dried formulation and does not need refrigeration. RPA can be used to replace PCR (Polymerase Chain Reaction) in a variety of laboratory applications and users can design their own assays.

Despite the many advances in this general field, existing nucleic acid amplification and detection methods and apparatus nevertheless suffer from various difficulties. For example, existing detection methods that determine assay results are prone to error, and existing nucleic acid amplification and detection apparatus are typically large, complex and costly.

It is desired to provide a nucleic acid amplification and detection apparatus and method that alleviate one or more difficulties of the prior art, or that at least provide a useful alternative.

SUMMARY

In accordance with some embodiments of the present invention, there is provided a nucleic acid amplification and detection apparatus, including:
- a support configured to receive a plurality of reaction vessels containing respective samples of one or more nucleic acids to be amplified, the support being rotatable about an axis of rotation and the reaction vessels being received in the support at respective receiving locations distributed about the axis of rotation;
- a temperature control component thermally coupled to the support and configured to control the temperature of the support in order to amplify the nucleic acids contained in the reaction vessels while received in the support;
- one or more measurement components configured to measure one or more characteristics of the nucleic acids within the reaction vessels at respective measurement locations distributed about the axis of rotation;
- an actuator coupled to the support and configured to rotate the support about the axis of rotation; and
- a sample position controller coupled to the actuator and being configured to rotate the support about the axis of rotation so as to position a selected one of the plurality of reaction vessels to a selected one of the measurement locations to allow a corresponding one of the measurement components to perform a corresponding measurement on the corresponding sample.

In some embodiments, the one or more measurement components include a plurality of measurement components configured to measure respective characteristics of the nucleic acids within the reaction vessels at respective measurement locations distributed about the axis of rotation.

In some embodiments, the measurement components include one or more optical measurement components configured to measure respective optical characteristics including optical absorption, reflection, luminance output, and/or fluorescence.

In some embodiments, the optical measurement components include optical measurement components configured to measure multiple channels of fluorescence, reflectance or transmission, or combinations thereof.

In some embodiments, the sample position controller is configured to selectively cause the actuator to rotate the support about the axis of rotation in an oscillatory manner to cause mixing of the contents of the reaction vessels.

In some embodiments, the nucleic acid amplification and detection apparatus includes an ultrasonic transducer component configured for selective coupling to a selected one of the reaction vessels to cause mixing of the contents of the selected reaction vessel.

In some embodiments, the ultrasonic transducer component is configured to support the selected reaction vessel in a spaced arrangement relative to the support to inhibit the coupling of ultrasonic energy to the support.

In some embodiments, the nucleic acid amplification and detection apparatus includes a sample identification component configured to identify a selected sample based on an identifier associated with the corresponding reaction vessel.

In some embodiments, the sample identification component includes at least one of a barcode reader, an RFID sensor, and an imaging device.

In some embodiments, the sample identification component includes an imaging device, and the sample identification component is further configured to acquire an image of the contents of the reaction vessel and to process the acquired image to confirm the reagents therein.

In some embodiments, the temperature control component is thermally coupled to the support across a gap therebetween. In some embodiments, the gap includes a thermally conductive fluid therebetween. In some embodiments, the thermally conductive fluid is a magnetic fluid retained within the gap by one or more magnets.

In some embodiments, the nucleic acid amplification and detection apparatus includes one or more magnets arranged about the support at respective different heights, such that when the support is rotated, paramagnetic beads within a reaction vessel in the support move past the magnets, causing the beads to oscillate correspondingly within the reaction vessel.

In some embodiments, the nucleic acid amplification and detection apparatus includes a processing component configured to process sensor data representing the measured characteristics to determine an assay result for the nucleic acids within the reaction vessels.

In some embodiments, the processing component is configured to:
- receive signal data representing assay measurements of a sample containing at least one nucleic acid at respective times during amplification of the at least one nucleic acid;
- process said signal data to generate second derivative data representing values of a second derivative of said signal data with respect to time;
- process said second derivative data to determine whether at least one of the second derivative values exceeds a predetermined second derivative threshold value;

process said second derivative data to determine a crossover time at which the second derivative of said signal data crosses zero after having exceeded the second derivative threshold value;

process said signal data to generate first derivative data representing a first derivative of said signal data with respect to time at the crossover time; and generate assay result data representing a result of the assay, the result being-determined on the basis of: (i) whether the predetermined second derivative threshold value was exceeded, and (ii) the first derivative of said signal with respect to time at the crossover time.

In some embodiments, the processing component is configured to:

receive signal data representing assay measurements of a sample containing at least one nucleic acid at respective times during amplification of the at least one nucleic acid;

process said signal data to generate second derivative data representing values of a second derivative of said signal data with respect to time;

process said second derivative data to determine whether at least one of the second derivative values exceeds a predetermined second derivative threshold value;

process said second derivative data to determine whether the second derivative of said signal data crosses zero after having exceeded the second derivative threshold value;

process said second derivative data to determine which of the second derivative values are positive;

determine a width or integrated area of the positive second derivative values;

compare the width or integrated area of the positive second derivative values with a further predetermined threshold value; and generate assay result data representing a result of the assay, the result being determined on the basis of: (i) whether the predetermined second derivative threshold value was exceeded, (ii) whether the second derivative of said signal crosses zero after having exceeded the second derivative threshold value, and (iii) whether the width or integrated area of the positive second derivative values exceeds the further predetermined threshold value.

In accordance with some embodiments of the present invention, there is provided a nucleic acid amplification and detection method, including:

receiving signal data representing assay measurements of a sample containing at least one nucleic acid at respective times during amplification of the at least one nucleic acid;

processing said signal data to generate second derivative data representing values of a second derivative of said signal data with respect to time;

processing said second derivative data to determine whether at least one of the second derivative values exceeds a predetermined second derivative threshold value;

processing said second derivative data to determine a crossover time at which the second derivative of said signal data crosses zero after having exceeded the second derivative threshold value;

processing said signal data to generate first derivative data representing a first derivative of said signal data with respect to time at the crossover time;

generating assay result data representing a result of the assay, the result being determined on the basis of: (i) whether the predetermined second derivative threshold value was exceeded, and (ii) the first derivative of said signal with respect to time at the crossover time; and outputting the assay result data.

In accordance with some embodiments of the present invention, there is provided a nucleic acid amplification and detection method, including:

receiving signal data representing assay measurements of a sample containing at least one nucleic acid at respective times during amplification of the at least one nucleic acid;

processing said signal data to generate second derivative data representing values of a second derivative of said signal data with respect to time;

processing said second derivative data to determine whether at least one of the second derivative values exceeds a predetermined second derivative threshold value;

processing said second derivative data to determine whether the second derivative of said signal data crosses zero after having exceeded the second derivative threshold value;

processing said second derivative data to determine which of the second derivative values are positive;

determining a width or integrated area of the positive second derivative values;

comparing the width or integrated area of the positive second derivative values with a further predetermined threshold value;

generating assay result data representing a result of the assay, the result being determined on the basis of: (i) whether the predetermined second derivative threshold value was exceeded, (ii) whether the second derivative of said signal crosses zero after having exceeded the second derivative threshold value, and (iii) whether the width or integrated area of the positive second derivative values exceeds the further predetermined threshold value; and outputting the assay result data.

In accordance with some embodiments of the present invention, there is provided a computer-readable storage medium having stored thereon programming instructions or configuration data that, when executed by at least one processor, causes the processor to execute any one of the above methods.

In accordance with some embodiments of the present invention, there is provided a nucleic acid detection apparatus configured to execute any one of the above methods.

BRIEF DESCRIPTION OF THE DRAWINGS

Some embodiments of the present invention are hereinafter described, by way of example only, with reference to the accompanying drawings, wherein.

DETAILED DESCRIPTION

Figure 1:
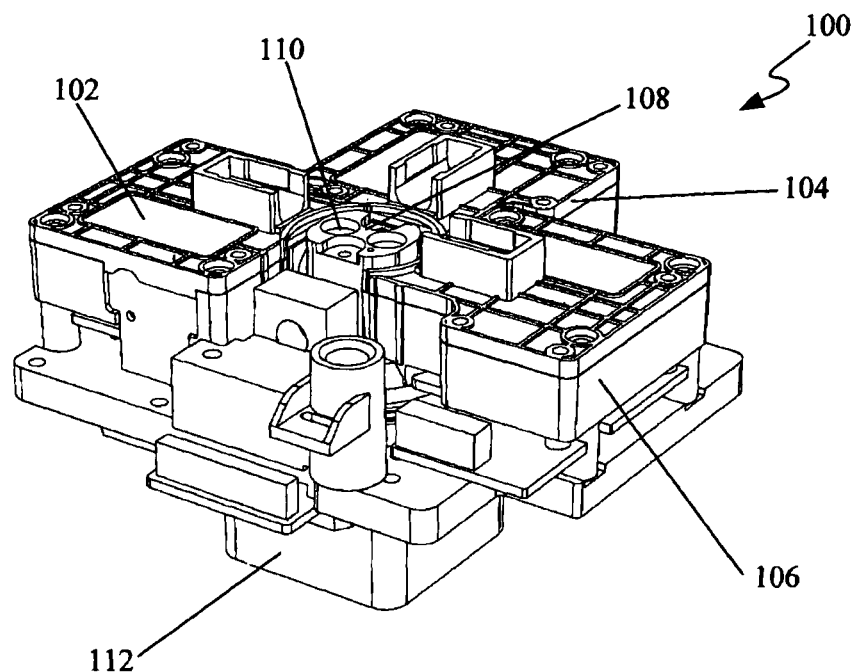
FIGS. 1 to 4 are isometric, plan, cut-away, and exploded views, respectively, of an assembly of a nucleic acid amplification and detection apparatus.

The described embodiments of the present invention include a nucleic acid amplification and detection apparatus that combines, in a single integrated instrument, nucleic acid amplification with measurement of the resulting amplification products during and/or following amplification. In various embodiments, the apparatus provides temperature control suitable for a DNA amplification reaction within removable reaction vessels using isothermal and/or thermocycled protocols, together with diagnostic or measurement components that are used to measure characteristics of the samples while still contained within the same removable reaction vessels. In particular, the apparatus allows the optical and/or electromagnetic characteristics of amplified nucleic acid samples to be measured while the controlled temperature environment is maintained such that it can be used as biomedical, environmental, food safety, or veterinary applications.

The apparatus includes a support configured to receive a plurality of reaction vessels containing respective samples of one or more nucleic acids to be amplified. In some embodiments, the support is configured to receive a disposable component that supports or otherwise includes or incorporates the reaction vessels. In the described embodiments, the reaction vessels are in the form of standard sample tubes such as those used for PCR, but this need not be the case in other embodiments. The support is rotatable about an axis of rotation and the reaction vessels are supported at respective receiving locations distributed about the axis of rotation. A temperature control component thermally coupled to the support is configured to control the temperature of the support and hence the samples contained in the reaction vessels, thereby allowing the nucleic acids contained in the reaction vessels to be amplified.

In order to perform measurements on the sample during and/or following nucleic acid amplification, the apparatus includes measurement components configured to measure one or more characteristics of the nucleic acids within the reaction vessels at respective measurement locations distributed about the axis of rotation. The measurement components arranged in this manner are thus also referred to herein as 'measurement stations'. This arrangement allows any one of the reactions vessels to be moved to any one of the measurement locations by simply rotating the support so that the selected reaction vessel is positioned at the selected measurement location. This is achieved by the apparatus including a sample position controller and associated actuator configured to rotate the support about the axis of rotation so as to move the selected reaction vessel to the selected measurement location. This allows the corresponding measurement component to measure one or more characteristics of the nucleic acids within the reaction vessel.

For example, a sample of interest can be divided into one or more reaction vessels so that the apparatus can be used to amplify the nucleic acids(s) in the divided sample and to measure multiple test and control reactions, displaying the results of these multiple tests to a user.

Use of fluorescence as a detection signal can provide good sensitivity, and where the measurement components include multiple fluorescence detectors configured to detect respective non-overlapping wavelength ranges so as not to interfere with one another, multiple channels of test and/or control reactions can be incorporated within a single reaction vessel. The measurement components can be configured to measure optical absorption, reflection, luminance output, and/or fluorescence.

The rotatable support arrangement allows measurement components configured to perform different sample measurements to be arranged around the support so that any of the reaction vessels in the support can be moved into position for a selected measurement on demand. These measurements may include, for example and inter alia, multiple channels of fluorescence, reflectance or transmission, combinations of these. Other measurements can be additionally or alternatively included, if required. Thus multiple measurement stations can access each sample, allowing a combination of measurements to be provided for each reaction vessel.

The supporting of the consumable or reaction vessels in the rotatable support also allows the contents of the reaction vessels to be mixed by rapid oscillatory rotation of the support under control of the sample position controller and associated actuator. The rotary oscillation induces mixing flows and disruption to the fluid within each reaction vessel, thereby improving the degree of reaction, reaction times and uniformity of measurements within the apparatus.

The mixing can be enhanced by including magnetic beads and/or other forms of disruptive features within each reaction vessel. For example, in some embodiments permanent magnets are fixed at locations just beyond the outer periphery of the support and arranged circumferentially about the rotation axis and at different alternating heights, so that when the support is rotated, paramagnetic beads within a reaction vessel move past the magnets at alternating heights, causing the beads to oscillate correspondingly up and down within the reaction vessel.

Figure 2:
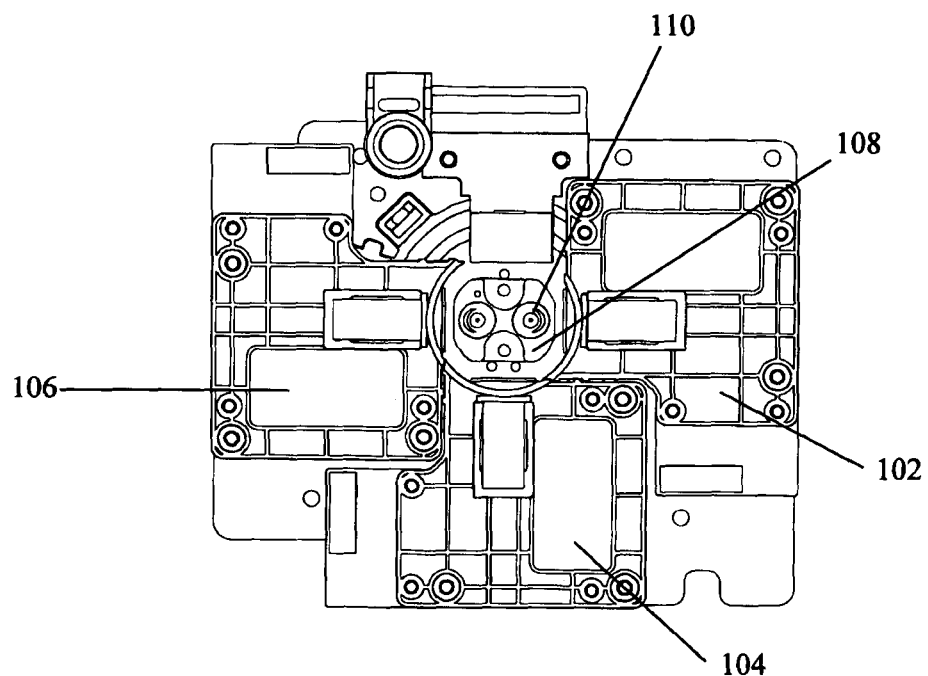
Figure 3:
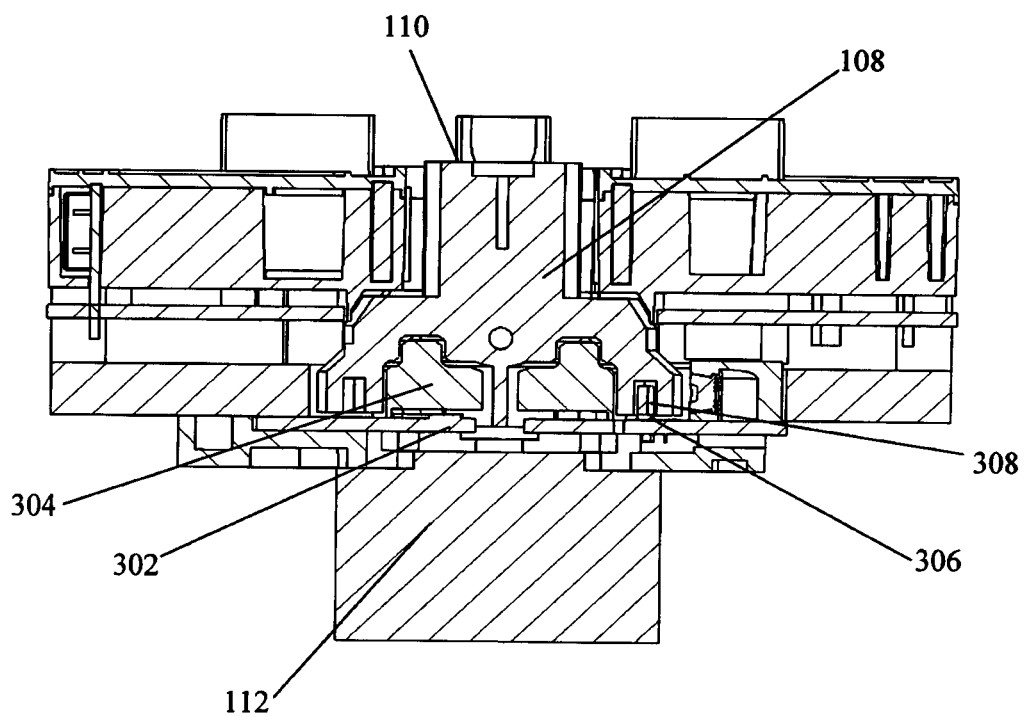
Figure 4:
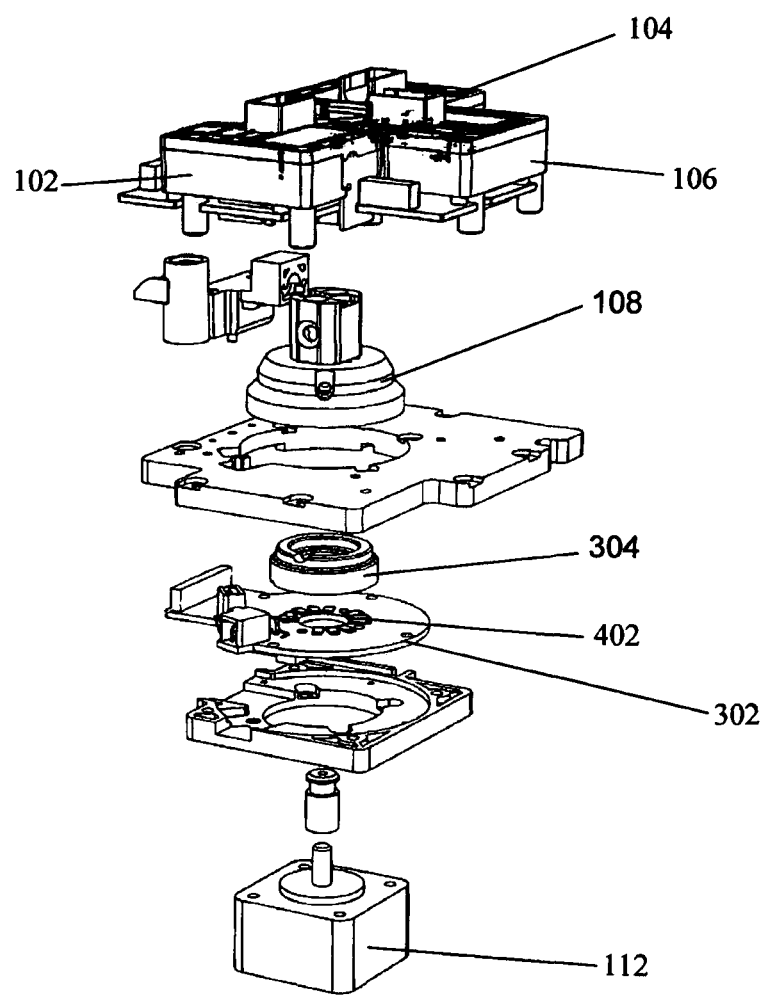

FIGS. 1 to 3 show an assembly 100 of an embodiment in which the apparatus includes three optical measurement stations 102, 104, 106 arranged about a support 108 that includes two openings 110 configured to receive respective reaction vessels. The support 108 is cylindrically symmetric about its axis of rotation, and is composed of a material having a high thermal conductivity such as aluminium or copper, for example.

In some embodiments (not shown), the heating and temperature control of the support is achieved using electrical heating elements such as resistors, and at least one temperature sensor embedded in or otherwise attached to the support. Electrical connections to these heating elements and temperature sensor are by way of cable connections or slip rings. In embodiments with cable connections, the rotation of the support is limited in angular travel.

In contrast to these arrangements, the embodiment shown in FIGS. 1 to 4 uses non-contact means to control the temperature of the support 108. As shown in the cut-away view of FIG. 3 and the exploded view of FIG. 4, the assembly 100 includes a printed circuit board (PCB) 302 having resistive heater elements 402 mounted thereon in a circular arrangement to provide heating to a metallic annular ring 304 rigidly mounted to the PCB 302.

The ring 304 is mounted within a complementary and generally annular cavity in a generally circular lower portion or skirt of the support 108 with a small gap therebetween. The ring 304 and the lower portion of the support 108 are in close mutual proximity over a large common surface area of the gap to improve the thermal transfer from the ring 304 to the support 108. In other embodiments, this thermal transfer can be achieved by a thermal gap similar to that described above but with different shapes (e.g., as a flat plate with a gap to a flat underside of the support), or alternatively by a sliding thermally conductive contact. The thermal coupling is such that a desired amplification temperature in the range of about 35-65° C. can be reached within a period of about ten minutes or less from a starting temperature around room temperature or, in the case of PCR, from one of the PCR operating temperatures.

In embodiments where the thermal transfer is across a gap, this gap may be filled with air or a thermally conductive fluid such as a thermally conductive grease or silicon oil retained within the gap by a seal. In some embodiments, a magnetic fluid is retained within this gap using magnets disposed on either or both sides of the gap.

The cut away view of FIG. 3 also shows a non-contact temperature sensor 306 mounted on the printed circuit board (PCB) 302 to provide feedback to a standard temperature control circuit, which can also be on the PCB 302 or alternatively external to the assembly 100. The temperature sensor 306 measures the temperature of the rotating support 108 but is mounted to the fixed printed circuit board (PCB) 302. The temperature sensor 306 is connected to an annular member or vane 308 that is disposed within an annular channel in the lower portion of the support 108 with a small gap therebetween. This arrangement provides good thermal coupling to the sensor 306 from the support 108 across the small gap into the metallic vane 308 attached to the sensor 306.

Where both the heater elements 402 and the feedback temperature sensor 306 are connected to electronic circuits and additionally the heater elements 402 are controlled by a microprocessor or analogue control circuit, accurate temperature control strategies can be implemented. For example proportional, integral, differential, (PID) control can be used to accurately drive and stabilise the support 108 and the sensor 306 to a desired temperature set point.

In other embodiments, alternative types of non-contact temperature sensors can be used. For example, a non-contact optical or infra-red temperature sensor such as the Melexis MLX90615 Infra Red Thermometer sensor are used in some embodiments. In some embodiments, multiple temperature sensors with different characteristics are used to optimise the temperature control strategy for rapid heat up and transitions combined with good steady state temperature accuracy. In some embodiments, air flow and/or Peltier cell elements are used to actively cool the support 108 to provide a rapid temperature transition to lower temperatures.

Self Test Capacity

In some embodiments, additional openings in the support are provided to receive calibration or reference samples with specific optical characteristics. This allows a stepper motor/actuator 112 coupled to the support 108 to be controlled so that a sample to be measured or a reference target is positioned at a measurement station location. This can be used to self-calibrate or self-test the apparatus during power up or measurement cycles by comparing the measured reference values against know values for the reference target.

Ultrasonic Mixing

In some embodiments, the support can also be coupled to a vibrating mechanism or actuator such as an electromagnetic coil and slug. Actuation of this component can induce vibration in the reaction vessels mounted in the support. The excitation frequency can be in the range of Hz up to kHz. Where the excitation is above 20 kHz, it can be referred to as ultrasonic mixing. For high frequency or ultrasonic mixing, a piezoelectric actuator can be used.

In some embodiments, the apparatus includes an ultrasonic transducer configured so that the support can rotate the reaction vessel so that the ultrasonic transducer can contact it through an opening in the support, with the ultrasonic transducer slightly lifting the reaction vessel so that it is not fully supported by the support. This allows efficient ultrasonic excitation of each reaction vessel only (i.e., without exciting the support itself) while otherwise allowing the reaction vessel to be seated in good thermal contact at other rotation positions and associated measurement stations.

Barcode Reading and Image Analysis

In some embodiments, the apparatus includes a barcode reader, RFID reader or an image sensor, and the support can be rotated to position a selected reaction vessel or associated disposable plastic assembly carrying or forming the vessel such that an attached label or feature is positioned in front of the barcode reader, RFID reader or image sensor. Where an image sensor is used, this can also be employed to confirm that the sample and reaction vessel or the disposable assembly that carries the reaction vessels have the correct reagents added, are assembled correctly, and are functional.

Figure 5:
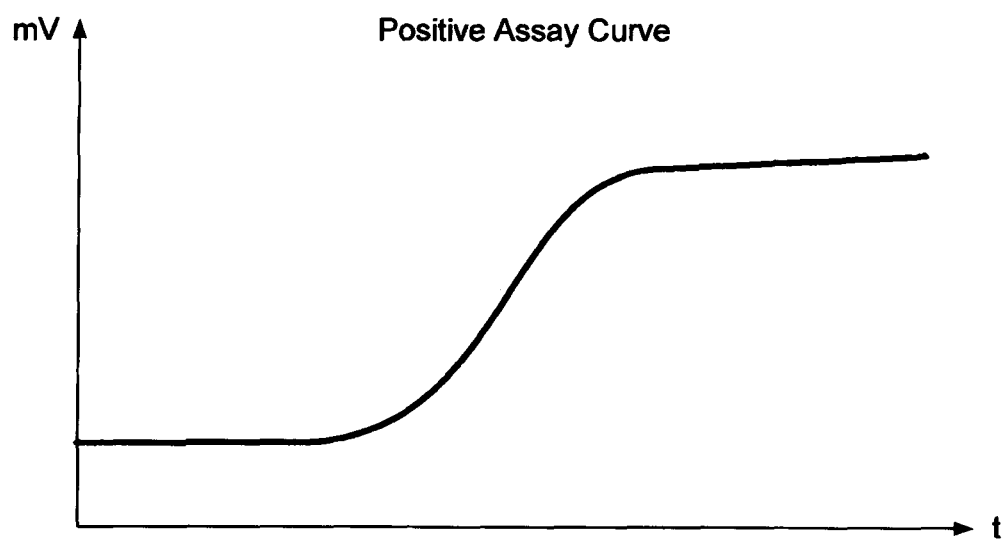
FIG. 5 is a schematic graph of a typical nucleic acid assay measurement as a function of time during amplification of the nucleic acid.

In some embodiments, the apparatus includes a processing component that uses the measured outputs from a sample over time to determine a diagnostic test result. FIG. 5 is a schematic illustration of a typical assay measurement (such as fluorescence) over time during nucleic acid amplification within the apparatus. Existing instruments use simple approaches such as a gradient threshold, a fixed or variable threshold for the assay at particular times in the amplification process. However, these prior art approaches are prone to error. In contrast, the apparatus uses an improved detection method that is more reliable than the standard methods used today.

The method involves receiving a signal (or, equivalently, signal data representing the signal) representing assay measurements of a sample during nucleic acid amplification, and generating second derivative data representing successive values of the second derivative of the signal (or signal data) with respect to time.

In the described embodiment, the assay test is considered to be asserted only if:
 (i) at least one of the second derivative values exceeds a predetermined positive second derivative threshold value; and
 (ii) the second derivative values cross zero after having exceeded the second derivative threshold value of (i), the time at which this occurs being referred to as the zero crossing time; and
 (iii) a measure of the width (e.g., the full width at half-maximum (FWHM)) or integrated second derivative values (the latter being equivalent to the first derivative value at the zero crossing time of (ii)) exceeds a further corresponding predetermined threshold value.

Figure 6:
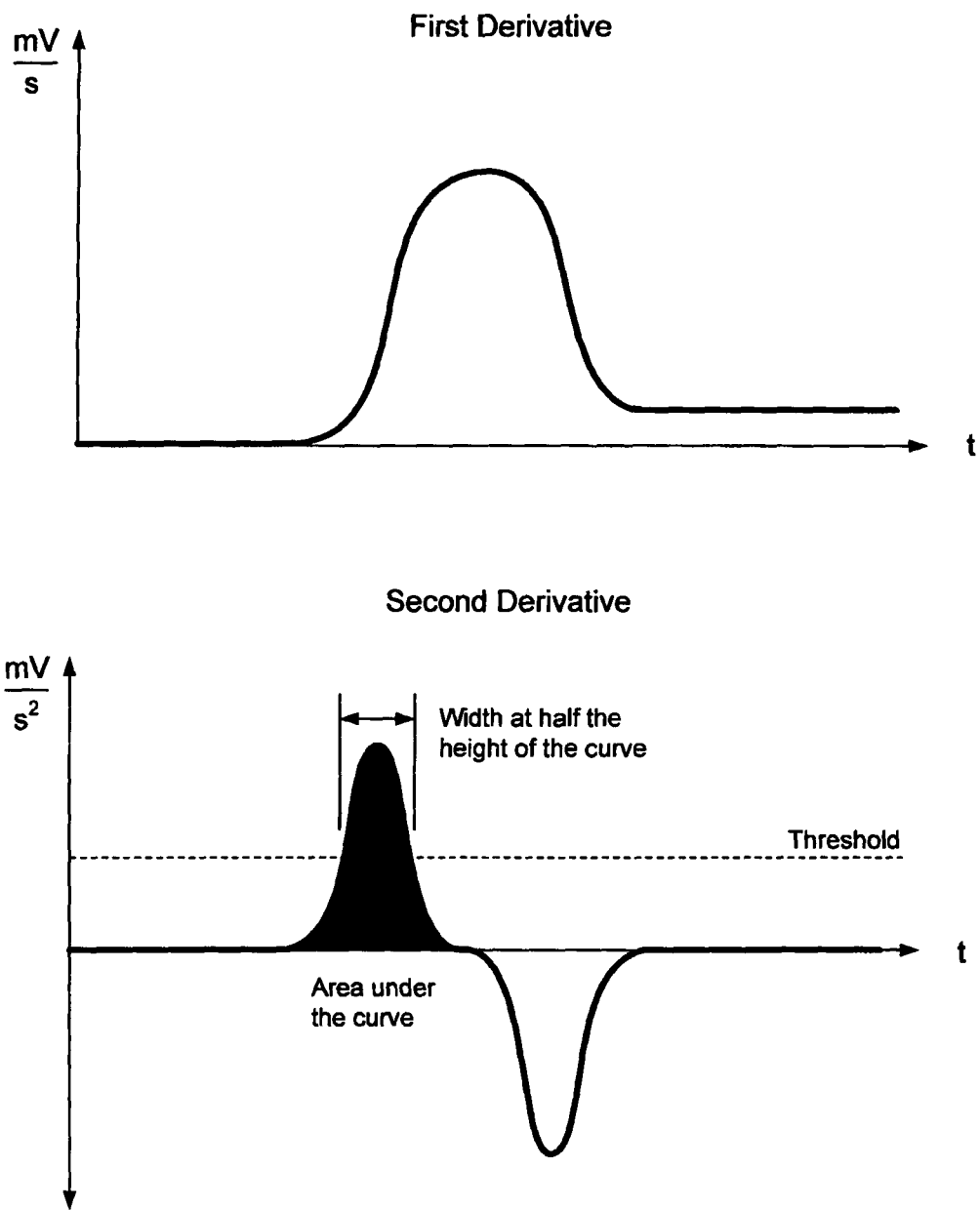
FIG. 6 includes schematic graphs of the first and second derivatives, respectively, with respect to time of the assay curve of FIG. 5.

Thus an assay curve is asserted if a positive going peak in the second derivative is present and has a height above a given threshold and a width or integrated area under its curve that exceeds a corresponding predetermined threshold value, as shown schematically in the lower part of FIG. 6.

In other embodiments, other characteristics of the second derivative values can be used as pass or fail criteria to determine whether the test result is asserted or not asserted or is possibly invalid. Suitable characteristics include the positive peak height, the area under the second derivative curve for the positive and negative going curves or the width of a peak in the second derivative curve, as shown in the lower part of FIG. 6.

Figure 7:
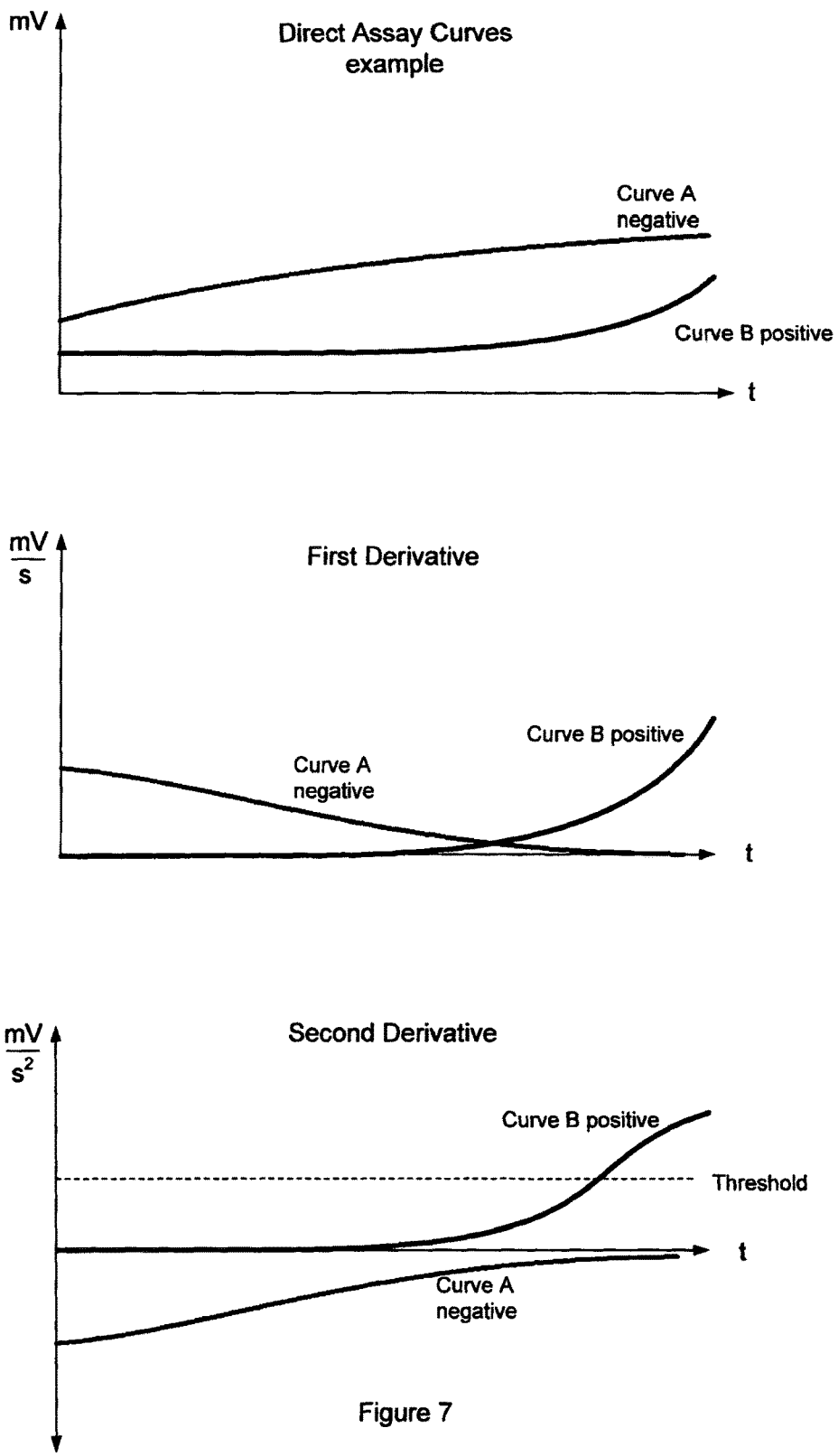
FIG. 7 includes schematic graphs of example assay measurement values and the first and second derivatives of those measured values, respectively, with respect to time.

An advantage of using a second derivative as an analysis method for determining a nucleic acid amplification diagnostic result is that it provides sensitivity to the essential exponential nature of some amplification methods and provides a reliable method to discriminate this within a test result. FIG. 7 provides an illustration of this. This method has particular application to (but is not limited to) isothermal nucleic acid reactions.

Figure 8:
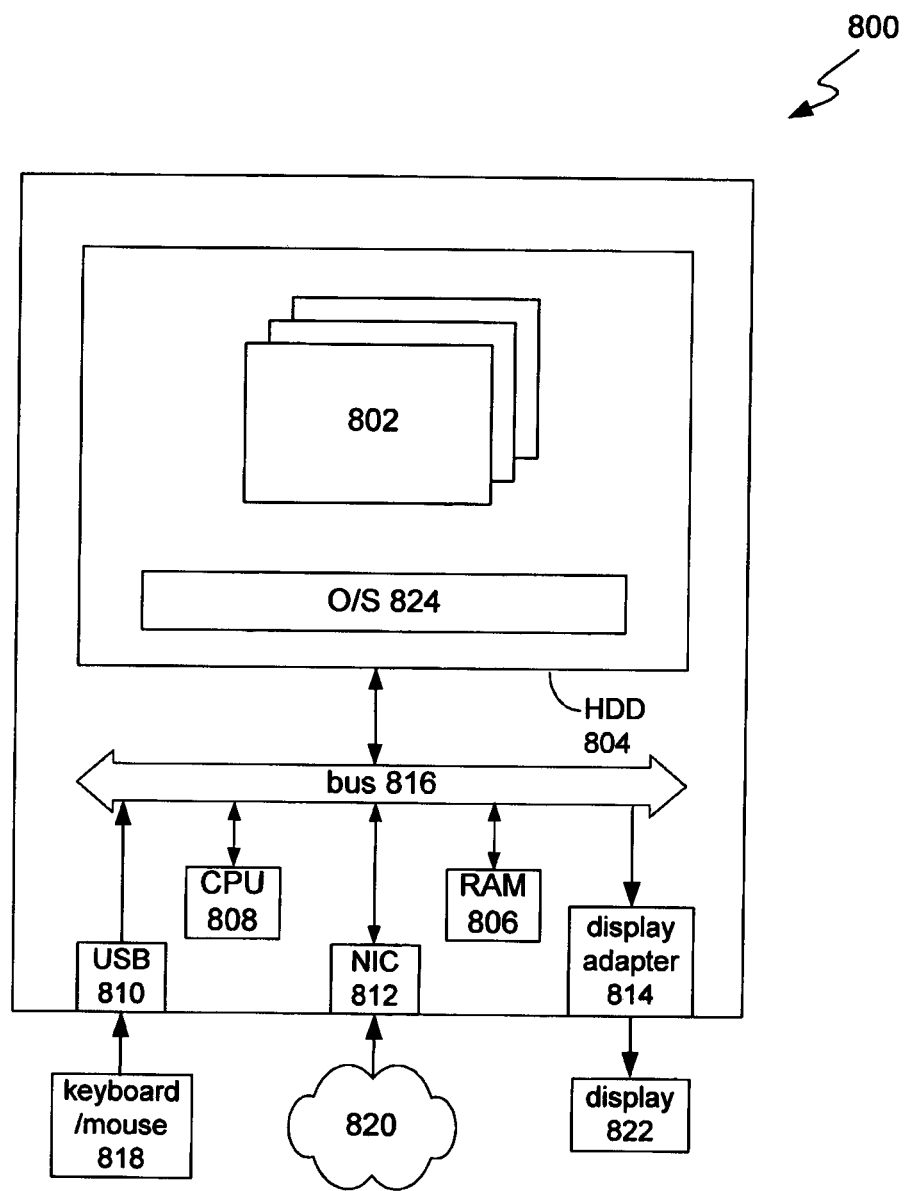
FIG. 8 is a block diagram of a processing component of the nucleic acid amplification and detection apparatus.

As will be apparent to those skilled in the art, the assay methods described above an be implemented by the processing component in a number of different ways. In some embodiments, the methods are implemented in the form of programming instructions of one or more software modules or components 802 stored on non-volatile (e.g., solid-state or hard disk) storage 804 associated with the processing component 800, as shown in FIG. 8.

The processing component 800 includes standard computer components, including random access memory (RAM) 806, at least one processor 808, and interfaces 810, 812, 814, all interconnected by a bus 816. The interfaces typically include universal serial bus (USB) interfaces 810, at least one of which may be connected to a keypad or keyboard 818 and optionally also a pointing device such as a mouse, a network interface connector (NIC) 812 which can be used to connect the processing component 800 to a communications network 820, if desired. The processing component 800 also includes a display adapter 814, which is connected to a display device such as an LCD panel display 822, and an operating system 824 such as Linux or Microsoft Windows.

In other embodiments, the methods can be stored in a PROM, EEPROM, or the like, or alternatively may be implemented in the form of configuration data for a field programmable gate arrays (FPGAs). In yet other embodiments, the methods may be implemented, either in part or in their entirety, in the form of one or more dedicated hardware components, such as application-specific integrated circuits (ASICs), for example.

Applications of the apparatus and methods described herein include diagnostic testing, particularly relating to a compact portable test instrument suitable for use in medical diagnostics at the Point-of-Care (POC) and in Physician's Office Laboratories (POL).

The described embodiments of the present invention include nucleic acid amplification and detection apparatus that are configured to receive only one or two measurement tubes contained within a single consumable assembly and are therefore suitable for portable, point of care, or other field applications. The described heated support/rotor arrangements enable multiple measurements, self-calibration and mixing functions to be performed with respect to a small number of reaction vessels or test tubes that are contained within in or are part of a disposable cartridge or vessel assembly. These features allow reduced complexity and make possible a compact, portable, and relatively low cost apparatus.

Notwithstanding the above, it will be apparent that in other embodiments a nucleic acid amplification and detection apparatus can in general be configured to receive any practical number of reaction vessels.

Many modifications will be apparent to those skilled in the art without departing from the scope of the present invention.

The invention claimed is:

1. A nucleic acid amplification and detection apparatus, including:
    a support configured to receive a plurality of reaction vessels containing respective samples of one or more nucleic acids to be amplified, the support being rotatable about an axis of rotation and the reaction vessels being received in the support at respective receiving locations distributed about the axis of rotation;
    a temperature control component thermally coupled to the support and configured to control the temperature of the support in order to amplify the nucleic acids contained in the reaction vessels while received in the support;
    a plurality of measurement components configured to measure respective characteristics of the nucleic acids within the reaction vessels at respective measurement locations distributed about the axis of rotation, wherein the measurement components are arranged radially outward with respect to the reaction vessels;
    a stepper motor coupled to the support and configured to rotate the support about the axis of rotation; and
    a sample position controller coupled to the stepper motor and being configured to:
    (i) cause the stepper motor to rotate the support about the axis of rotation in an oscillatory manner to cause mixing of the contents of the reaction vessels; and
    (ii) cause the stepper motor to selectively position and hold a selected one of the plurality of reaction vessels at a selected one of the plurality of measurement locations to allow a corresponding one of the plurality of measurement components to perform a corresponding measurement on a corresponding sample.

2. The nucleic acid amplification and detection apparatus of claim 1, wherein the measurement components include one or more optical measurement components configured to measure respective optical characteristics including optical absorption, reflection, luminance output, and/or fluorescence.

3. The nucleic acid amplification and detection apparatus of claim 2, wherein the optical measurement components include optical measurement components configured to measure multiple channels of fluorescence, reflectance or transmission, or combinations thereof.

4. The nucleic acid amplification and detection apparatus of claim 1, including an ultrasonic transducer component configured for selective coupling to a selected one of the reaction vessels to cause mixing of the contents of the selected reaction vessel.

5. The nucleic acid amplification and detection apparatus of claim 4, wherein the ultrasonic transducer component is configured to support the selected reaction vessel in a spaced arrangement relative to the support to inhibit the coupling of ultrasonic energy to the support.

6. The nucleic acid amplification and detection apparatus of claim 1, including a sample identification component configured to identify a selected sample based on an identifier associated with the corresponding reaction vessel.

7. The nucleic acid amplification and detection apparatus of claim 6, wherein the sample identification component includes at least one of a barcode reader, an RFID sensor, and an imaging device.

8. The nucleic acid amplification and detection apparatus of claim 6, wherein the sample identification component includes an imaging device, and the sample identification component is further configured to acquire an image of the contents of the reaction vessel and to process the acquired image to confirm the reagents therein.

9. The nucleic acid amplification and detection apparatus of claim 1, wherein the temperature control component is thermally coupled to the support across a gap therebetween.

10. The nucleic acid amplification and detection apparatus of claim 9, wherein the gap includes a thermally conductive fluid therebetween.

11. The nucleic acid amplification and detection apparatus of claim 10, wherein the thermally conductive fluid is a magnetic fluid retained within the gap by one or more magnets.

12. The nucleic acid amplification and detection apparatus of claim 1, including one or more magnets arranged about the support at respective different heights, such that when the support is rotated, paramagnetic beads within a reaction vessel in the support move past the magnets, causing the beads to oscillate correspondingly within the reaction vessel.

13. The nucleic acid amplification and detection apparatus of claim 1, including a processing component configured to process sensor data representing the measured characteristics to determine an assay result for the nucleic acids within the reaction vessels.

14. The nucleic acid amplification and detection apparatus of claim 13, wherein the processing component is configured to:
receive signal data representing assay measurements of a sample containing at least one nucleic acid at respective times during amplification of the at least one nucleic acid;
process said signal data to generate second derivative data representing values of a second derivative of said signal data with respect to time;
process said second derivative data to determine whether at least one of the second derivative values exceeds a predetermined second derivative threshold value;
process said second derivative data to determine a crossover time at which the second derivative of said signal data crosses zero after having exceeded the second derivative threshold value;
process said signal data to generate first derivative data representing a first derivative of said signal data with respect to time at the crossover time; and
generate assay result data representing a result of the assay, the result being determined on the basis of: (i) whether the predetermined second derivative threshold value was exceeded, and (ii) the first derivative of said signal with respect to time at the crossover time.

15. The nucleic acid amplification and detection apparatus of claim 13, wherein the processing component is configured to:
receive signal data representing assay measurements of a sample containing at least one nucleic acid at respective times during amplification of the at least one nucleic acid;
process said signal data to generate second derivative data representing values of a second derivative of said signal data with respect to time;
process said second derivative data to determine whether at least one of the second derivative values exceeds a predetermined second derivative threshold value;
process said second derivative data to determine whether the second derivative of said signal data crosses zero after having exceeded the second derivative threshold value;
process said second derivative data to determine which of the second derivative values are positive;
determine a width or integrated area of the positive second derivative values;
compare the width or integrated area of the positive second derivative values with a further predetermined threshold value; and
generate assay result data representing a result of the assay, the result being determined on the basis of: (i) whether the predetermined second derivative threshold value was exceeded, (ii) whether the second derivative of said signal crosses zero after having exceeded the second derivative threshold value, and (iii) whether the width or integrated area of the positive second derivative values exceeds the further predetermined threshold value.

16. The nucleic acid amplification and detection apparatus of claim 1, wherein the nucleic acid amplification and detection apparatus is a portable apparatus having a support configured to receive no more than two reaction vessels.

17. A nucleic acid amplification and detection apparatus, including:
a support configured to receive a plurality of reaction vessels containing respective samples of one or more nucleic acids to be amplified, the support being rotatable about an axis of rotation and the reaction vessels being received in the support at respective receiving locations distributed about the axis of rotation;
a temperature control component thermally coupled to the support and configured to control the temperature of the support in order to amplify the nucleic acids contained in the reaction vessels while received in the support;
a plurality of measurement components configured to measure respective characteristics of the nucleic acids within the reaction vessels at respective measurement locations distributed about the axis of rotation, wherein the measurement components are arranged radially outward with respect to the reaction vessels;
one or more magnets arranged about the support at respective different heights;
a stepper motor coupled to the support and configured to rotate the support about the axis of rotation; and
a sample position controller coupled to the stepper motor and being configured to:
(i) cause the stepper motor to rotate the support about the axis of rotation to cause oscillatory mixing of the contents of the reaction vessels such that, when the support is rotated, paramagnetic beads within a reaction vessel in the support move past the magnets, causing the beads to oscillate correspondingly within the reaction vessel; and
(ii) cause the stepper motor to selectively position and hold a selected one of the plurality of reaction vessels at a selected one of the plurality of measurement locations to allow a corresponding one of the plurality of measurement components to perform a corresponding measurement on a corresponding sample.

* * * * *